(12) United States Patent
Pandey et al.

(10) Patent No.: US 7,250,555 B2
(45) Date of Patent: Jul. 31, 2007

(54) METHODS FOR ENHANCING A PLANT STRESS RESPONSE

(75) Inventors: Girdhar K. Pandey, El Cerrito, CA (US); Rajeev Gupta, Berkeley, CA (US); Kyung-Nam Kim, Seoul (KR); Sheng Luan, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 866 days.

(21) Appl. No.: 10/098,306

(22) Filed: Mar. 15, 2002

(65) Prior Publication Data

US 2002/0166139 A1    Nov. 7, 2002

Related U.S. Application Data

(60) Provisional application No. 60/282,118, filed on Apr. 6, 2001.

(51) Int. Cl.
*C12N 15/09* (2006.01)
*C12N 15/82* (2006.01)
*A01H 5/00* (2006.01)

(52) U.S. Cl. ............... 800/289; 800/278; 800/298; 800/286; 435/468; 435/69.1

(58) Field of Classification Search ............... 800/278, 800/298, 289; 435/69.1, 468
See application file for complete search history.

(56) References Cited

U.S. PATENT DOCUMENTS 5,859,337 A * 1/1999 Gasser et al. ............... 800/298

FOREIGN PATENT DOCUMENTS

WO    WO 99/05902    *  2/1999
WO    WO 99/05902 A1    2/1999

OTHER PUBLICATIONS

Kudla, et al., "Genes for Calcineurin B-like Proteins in *Arabidopsis* are Differentially Regulated by Stress Signals," *Proc. Natl. Acad. Sci.*, vol. 96, pp. 4718-4723, USA, (Apr. 1999).
Liu, et al., "A Calcium Sensor Homolog Required for Plant Salt Tolerance," *Science*, vol. 280, pp. 1943-1945, (Jun. 19, 1998).
Kim, K. N. et al., "Interaction specificity of *Arabidopsis* calcineurin B-like calcium sensors and their target kinases," Plant Physiology, Dec. 2000, pp. 1844-1853, vol. 124.
Kudla, J. et al., "Genes for calcineurin B-like proteins in *Arabidopsis* are differentially regulated by stress signals," Proc. Natl. Acad. Sci. USA, Apr. 1999, pp. 4718-4723, vol. 96.
Shi, J. et al., "Novel protein kinases associated with calcineurin B-like calcium sensors in *Arabidopsis*," Plant Cell, Dec. 1999, pp. 2393-2405, vol. 11.

* cited by examiner

*Primary Examiner*—Medina A. Ibrahim
(74) *Attorney, Agent, or Firm*—Townsend and Townsend and Crew LLP (57) ABSTRACT

The invention provides novel methods useful for enhancing a stress response in plants. Specifically, the methods of the present invention are useful for increasing the tolerance of a plant to stresses such as hyperthermia, hypothermia, hyperosmolarity, hypoosmolarity, and wounds.

10 Claims, 4 Drawing Sheets

METHODS FOR ENHANCING A PLANT STRESS RESPONSE

CROSS-REFERENCES TO RELATED APPLICATIONS

This application claims the benefit of U.S. Provisional Patent Application Ser. No. 60/282,118, filed Apr. 6, 2001, which is herein incorporated by reference in its entirety.

STATEMENT AS TO RIGHTS TO INVENTIONS MADE UNDER FEDERALLY SPONSORED RESEARCH OR DEVELOPMENT

This invention was made with United States government support under Grant No. GM52826 awarded by the National Institutes of Health. The United States government has certain rights to this invention.

FIELD OF THE INVENTION

The present invention is directed to plant genetic engineering. In particular, it relates to methods for controlling a stress response in plants.

BACKGROUND OF THE INVENTION

Drought, cold, and salinity are critical environmental factors that limit crop productivity worldwide. In response to these stress signals, plants mount a number of defense reactions that increase the tolerance to the stressful conditions. The best-known molecular response is the activation of gene expression that leads to changes in protein profiles and physiological processes. The products of these so called "stress genes" are categorized in at least two functional groups. The first group includes metabolic enzymes required for biosynthesis of various osmo-protectants, chaperons, detoxifying enzymes, and other effector proteins that are directly involved in stress protection processes. The second category of gene products includes sensor/receptor proteins, protein kinases and phosphatases, enzymes involved in second messenger metabolism, and other components that constitute the signal transduction pathways connecting the stress signal to the cellular responses (Shinozaki et al., *Plant Physiol.* 115:327-334 (1997); Ingram et al., *Ann. Rev. Plant Physiol. Plant Mol. Biol.* 47:377-403 (1996); Bray, *Trends Plant Sci.* 2:48-54 (1997)).

In the stress signaling pathways, a number of studies implicate $Ca^{2+}$ as second messenger. First, elevation of cellular $Ca^{2+}$ is a rapid response to osmotic signals such as cold, drought, and salinity (Knight et al. *Plant J.* 12:1067-1078 (1997); Knight et al. *Plant Cell* 8:489-503 (1996); Knight et al. *Nature* 352:524-526 (1991)). Secondly, $Ca^{2+}$ is required for stress-induced gene expression in plants (Knight et al. *Plant Cell* 8:489-503 (1996)). Thirdly, $Ca^{2+}$ elevation is sufficient for activation of stress gene expression (Sheen, *Science* 274:1900-1902 (1996)). It is generally believed that $Ca^{2+}$ transmits the stress signal downstream in the pathway by interacting with protein sensors. These calcium sensors such as calmodulin (CaM), $Ca^{2+}$-dependent protein kinases (CDPK), bind $Ca^{2+}$ and interact with and regulate the activity of their target proteins (Sander et al *Plant Cell* 11:691-706 (1996); Roberts and Harmon, *Annu. Rev. Plant Physiol. Plant Mol. Biol.* 43:375-414 (1992); Zielinski, *Annu. Rev. Plant Physiol. Plant Mol. Biol.* 49:697-725 (1998)).

$Ca^{2+}$ serves as a second messenger in many stress signal transduction pathways (Sander et al. *Plant Cell* 11:691-706 (1996); Trewavas, *Plant Physiol.* 120:1-6 (1999); Bush, *Annu. Rev. Plant Physiol. Plant Mol. Biol.* 46:95-122 (1995)). However, the molecular mechanism for $Ca^{2+}$ action in plant cells is not well understood. The present invention demonstrates that a CBL calcium sensor is highly stress-responsive at the protein level. Constitutive expression of a CBL protein is sufficient for activation of multiple stress response pathways leading to enhanced tolerance to both salinity and osmotic stress in transgenic plants. This finding suggests that CBL proteins are an upstream regulator of stress gene expression and serves as a rate-limiting factor in stress response pathways.

One of the earliest responses to stress signals is elevation in cellular calcium in plants (Knight et al. *Plant J.* 12:1067-1078 (1997); Bush, *Annu. Rev. Plant Physiol. Plant Mol. Biol.* 46:95-122 (1995)). Later responses include changes in expression profiles of a large number of stress genes (Shinozaki and Yamaguchi-Shinozaki, *Plant Physiol.* 115:327-334 (1997); Ingram et al. *Ann Rev. Plant Physiol. Plant Mol. Biol.* 47:377-403 (1996); Bray, *Trends Plant Sci.* 2:48-54 (1997))). From calcium to gene expression, a number of intermediate components may play a role in the signaling process. These include calcium sensors such as CaM, CDPK, and AtCBL that are immediate downstream components following calcium changes (see, Roberts and Harmon *Annu. Rev. Plant Physiol. Plant Mol. Biol.* 43:375-414 (1992); Zielinski *Annu. Rev. Plant Physiol. Plant Mol. Biol.* 49:697-725 (1998); and Kudla et al. *Proc. Natl. Acad. Sci. USA* 96:4718-4723 (1999)).

It is generally believed that cellular $Ca^{2+}$ levels hold the key to the activation of stress response pathways. Normally, cellular $Ca^{2+}$ fluctuates below the "threshold value". Stress signals typically boost the $Ca^{2+}$ levels over the threshold leading to the activation of calcium sensors and the downstream components in the pathway. Consistent with this view, elevation of cellular $Ca^{2+}$ by ionophores is sufficient for activation of stress- and ABA-induced gene expression in the absence of stress or ABA application (Sheen, Science 274:1900-1902 (1996)). Levels of calcium sensors may alter the sensitivity to cellular $Ca^{2+}$. In the case of AtCBL1, its basal level is quite low and activation of the pathway increases the protein level. The stress-responsive increase may lower the threshold value for cellular $Ca^{2+}$ and serve as a feedback mechanism for increasing the sensitivity to stress signals. In transgenic plants, AtCBL1 protein levels are constantly high so that stress response pathways are turned on by basal $Ca^{2+}$ levels that are present under "normal" conditions. As a result, these plants are "hypersensitive" to stress signals.

A family of novel calcium sensors from *Arabidopsis* was recently described (Kudla et al. *Proc. Natl. Acad. Sci. USA* 96:4718-4723 (1999)). These proteins are similar to both the regulatory B subunit of calcineurin and the neuronal $Ca^{2+}$ sensor (NCS) in animals (Olafsson et al. *Proc. Natl. Acad. Sci USA* 92:8001-8005 (1995); Klee et al. *J Biol. Chem.* 273:13367-13370 (1998)). These unique plant $Ca^{2+}$ sensors have been referred to as *Arabidopsis* calcineurin B-like (AtCBL) proteins (Kudla et al. *Proc. Natl. Acad. Sci. USA* 96:4718-4723 (1999); Shi et al. *Plant Cell* 11:2393-2405 (1999); Kim et al. *Plant Physiol.* 124:1844-1853 (2000)). One member of the AtCBL gene family, AtCBL1, is highly inducible by stress signals including drought, cold, and wounding (Kudla et al. *Proc. Natl. Acad. Sci. USA* 96:4718-4723 (1999)), implicating AtCBL1 in plant response to multiple stress conditions. Another member, AtCBL4 or salt-overly sensitive 3 (SOS3) has been shown to play a role in salt resistance in *Arabidopsis* (Liu and Zhu, *Science* 280:1943-1954 (1998)). Like calmodulin (CaM), calcineurin B, and NCS, the AtCBL family calcium sensors are small $Ca^{2+}$-binding proteins that do not have enzymatic activity by themselves and function as $Ca^{2+}$-sensors by interacting with other signaling proteins. Using yeast two-hybrid screening, Shi et al. *Plant Cell* 11:2393-2405 (1999) identified a group of novel protein kinases (CIPKs) as target proteins for AtCBL1. Halfter et al. *Proc. Natl. Acad. Sci. USA* 97:3735-3740 (2000) describes a similar group of protein kinases (SIP) as targets for AtCBL4/SOS3. CIPK/SIP represents a new subclass of protein kinases that are related to SNF1/AMPK family in the kinase domain but contain a unique regulatory domain in the C-terminal non-kinase region. The C-terminal regulatory domain is required and sufficient for interaction with AtCBL $Ca^{2+}$ sensors (Shi et al. *Plant Cell* 11:2393-2405 (1999); Kim et al. *Plant Physiol.* 124:1844-1853 (2000); Halfter et al. *Proc. Natl. Acad. Sci. USA* 97:3735-3740 (2000)). Taken together, these studies suggest that the AtCBL family of calcium sensors functions by interacting with a family of protein kinases. The specificity of interaction between the AtCBL calcium sensors and their target kinases is important in determining their specific function in plants (Kim et al. *Plant Physiol.* 124:1844-1853 (2000)).

To date, only a few studies have been reported on the function of these calcium sensors in stress-induced gene expression. One study shows that constitutive activation of specific CDPK isoforms is sufficient for expression of ABA-induced genes without ABA treatment (see, Sheen *Science* 274:1900-1902 (1996)). Overexpression of two pathogen-inducible CaM genes activates pathogen-response pathway in a pathogen-independent manner (see, Heo et al. *Proc. Natl. Acad. Sci. USA* 96:766-771 (1999)). These studies suggest that CaM and CDPK are upstream of pathogen- and ABA-induced gene expression in the signaling pathways.

In light of the above, it is thought that CBL genes are involved in controlling a plant stress response. It is not known, however, whether control of the expression of the genes would be useful in controlling a plant stress response. The present invention addresses these and other needs in the prior art.

BRIEF SUMMARY OF THE INVENTION

The present invention provides methods of modulating a stress response in plants. The methods generally involve providing a plant a recombinant expression cassette containing a CBL (calcineurin B-like) nucleic acid linked to a plant promoter. The present invention employs the discovery that CBL protein levels are low under normal conditions and highly increased upon stress.

In one embodiment of the invention, a method of enhancing stress tolerance in a plant is provided. An expression cassette comprising a plant promoter operably linked to a heterologous CBL polynucleotide is introduced into the plant. The expression cassette may be introduced into the plant through a sexual cross.

The heterologous CBL polynucleotide may encode a CBL polypeptide. The CBL polypeptide may have an amino acid sequence as shown in SEQ ID NO:2. The heterologous CBL polynucleotide may be SEQ ID NO:1.

In some embodiments, expression of the CBL nucleic acids of the invention is used to enhance expression of an endogenous CBL gene or gene product activity. In these embodiments, the nucleic acids are used to modulate a stress response in a plant. Preferably, the stress response is modulated to increase tolerance to such stresses as drought, hyperthermia, hypothermia including cold or freezing, hyperosmolarity or hypoosmolarity such as that induced by salts, or by wounds.

In some embodiments, the stress response is modulated by increasing the presence of one or more transcription factors. Representative transcription factors active in some stress response pathways according to the present invention include but are not limited to DREB1A and DREB2A.

In the expression cassettes, the plant promoter may be a constitutive promoter, for example, the CaMV 35S promoter. Alternatively, the promoter may be a tissue-specific or an inducible promoter. For instance, the promoter sequence from the CBL genes disclosed here can be used to direct expression in relevant plant tissues.

Another embodiment of the present invention is a transgenic plant comprising an expression cassette comprising a plant promoter operably linked to a heterologous CBL polynucleotide. It will be readily apparent to those of skill in the art that almost any plant species may be so transformed. It will also be readily apparent to those of skill in the art that such transformed plants may be easily engineered to produce high levels of a CBL either with or without induction by an external stimulus.

BRIEF DESCRIPTION OF THE DRAWINGS

FIG. 1 demonstrates stress and abscisic acid (ABA)-induction of AtCBL1 protein in *Arabidopsis* plants. Plants were treated with various stress conditions and total protein was extracted at different time points. Each lane was loaded with 30 µg protein for SDS-PAGE procedure followed by western blot analysis using anti-AtCBL1 antibody. For treatments with cold, ABA, salt, mannitol, and water, the time points are 0, 4, 8, 24 and 48 h (lanes 1-5). For wounding treatment, the time points are 0, 20' minutes, 1 hour, 2 hours, 4 hours and 8 hours (lanes 1-6).

FIG. 3 demonstrates stress-independent activation of stress-responsive genes in AtCBL1-expressing plants. (a) Expression pattern of RD29A, DREB1A and DREB2A genes in wild type *Arabidopsis* plants in response to various stress conditions. (b) RD29A expression in control (lanes 1 and 2) and eight AtCBL1-expressing lines (lanes 3-10) before (upper blot) and after (lower blot) cold treatment. Similar blots were probed with DREB1A (c) or DREB2A (d) to show the expression pattern of these genes in the same control and AtCBL1-expressing lines before and after cold treatment.

FIG. 5 represents a molecular model of AtCBL1 function in stress signal transduction. AtCBL1 is an upstream component in multiple stress response pathways. These pathways utilize $Ca^{2+}$ as a second messenger that in turn activates AtCBL1. AtCBL1 interacts with its target proteins including CIPKs (Kim et al. *Plant Physiol.* 124:1844-1853 (2000); Liu et al., *Science* 280:1943-1954 (1998)). CIPKs and possibly other targets transmit the signal further downstream to transcriptional factors that activate expression of stress genes including DREB1A and DREB2A transcriptional factors. DREB1A and DREB2A activate the expression of target genes including RD29A.

DETAILED DESCRIPTION OF THE INVENTION

The phrase "enhancing stress tolerance" is meant to encompass directly or indirectly increasing or decreasing transcription or translation of a gene or gene product involved in enhancing a plant's ability to adapt to a stress thereby increasing tolerance to the stress or decreasing damage caused by the stress. The term is meant to encompass increasing or decreasing the transcription or translation of such "stress genes" as metabolic enzymes required for biosynthesis of various osmo-protectants, chaperons, detoxifying enzymes, and other effector proteins that are directly involved in stress protection processes and such "stress genes" as sensor/receptor proteins, protein kinases and phosphatases, enzymes involved in second messenger metabolism, and other components that constitute the signal transduction pathways connecting the stress signal to the cellular responses.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of the same. The class of plants which can be used in the methods of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

A "CBL nucleic acid" or "CBL polynucleotide sequence" of the invention is a subsequence or full length polynucleotide sequence of a gene which encodes a polypeptide involved in effecting a stress response in plants. An exemplary nucleic acid of the invention is the CBL1 sequence disclosed below. CBL1 polynucleotides of the invention are defined by their ability to hybridize under defined conditions to the exemplified nucleic acids or PCR products derived from them. A CBL1 polynucleotide is typically at least about 30-40 nucleotides to about 4500 nucleotides, usually about 3800 to 4000 nucleotides in length. The nucleic acids contain coding sequence of from about 100 to about 28000 nucleotides, often from about 500 to about 1000 nucleotides in length.

In the case of both expression of transgenes and inhibition of endogenous genes (e.g., by antisense, or sense suppression), one of skill will recognize that the inserted polynucleotide sequence need not be identical, but may be only "substantially identical" to a sequence of the gene from which it was derived. As explained below, these substantially identical variants are specifically covered by the term CBL1 nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "CBL nucleic acid". In addition, the term specifically includes those sequences substantially identical (determined as described below) with a CBL polynucleotide sequence disclosed here and that encode polypeptides that are either mutants of wild type CBL polypeptides or retain the function of the CBL polypeptide (e.g., resulting from conservative substitutions of amino acids in the CBL polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers et al., *Computer Applic. Biol. Sci.* 4:11-17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60% identity, preferably 65%, 70%, 75%, 80%, 85%, 90%, or 95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith et al., *Adv. Appl. Math.* 2:482 (1981), by the homology alignment algorithm of Needleman et al., *J. Mol. Biol.* 48:443 (1970), by the search for similarity method of Pearson et al., *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng et al., *J. Mol. Evol.* 35:351-360 (1987). The method used is similar to the method described by Higgins et al., *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al. *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see, Henikoff and Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin et al., *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising CBL nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

I. Introduction

The present invention provides methods of modulating a stress response in plants. The methods generally involve providing a plant a recombinant expression cassette containing a CBL nucleic acid linked to a plant promoter.

In some embodiments, expression of the CBL nucleic acids of the invention are used to enhance expression of an endogenous CBL gene or gene product activity. In these embodiments, the nucleic acids are used to enhance stress tolerance in a plant. Preferably, the stress tolerance is enhanced to increase tolerance to such stresses as hyperthermia, hypothermia such as cold or freezing, hyperosmolarity or hypoosmolarity such as that induced by salts, or to wounds.

In some embodiments, the stress tolerance is enhanced by increasing the presence of one or more transcription factors. Representative transcription factors active in some stress response pathways according to the present invention include but are not limited to DREB1A and DREB2A.

In the expression cassettes, the plant promoter may be a constitutive promoter, for example, the CaMV 35S promoter. Alternatively, the promoter may be a tissue-specific or an inducible promoter. For instance, the promoter sequence from the CBL genes disclosed here can be used to direct expression in relevant plant tissues.

The invention also provides recombinant plants transformed with such a recombinant expression cassette containing a CBL nucleic acid linked to a plant promoter. It will be readily apparent that almost any plant species may be so transformed. It will also be readily apparent that such transformed plants may be easily engineered to produce high levels of a CBL either with or without induction by an external stimulus.

Figure 5:
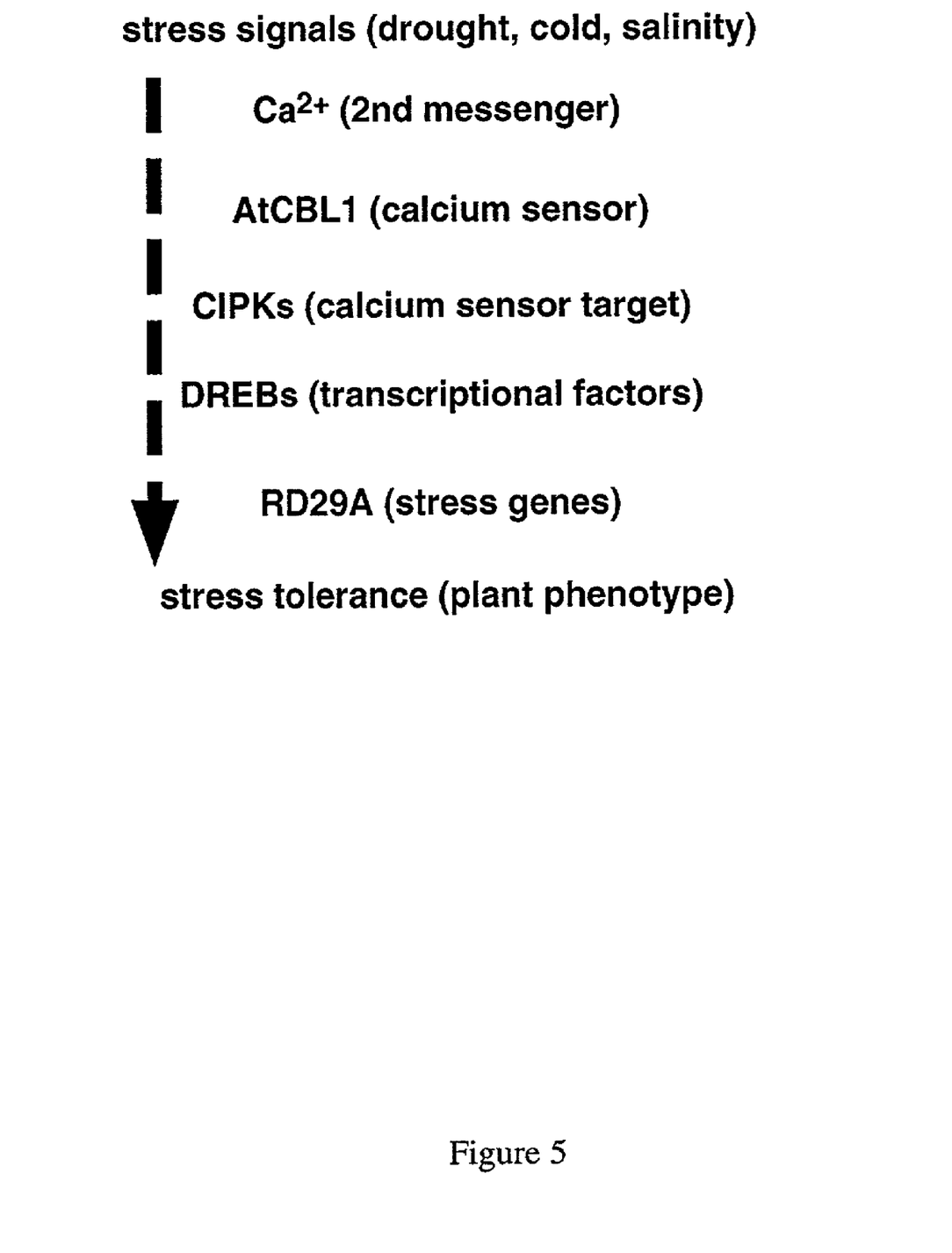

The present data demonstrate that elevated expression of a CBL gene activates the expression of both DREB1A and DREB2A, transcriptional factors that regulate a number of stress genes including RD29A. Because DREB1A and DREB2A are regulated by different stress signals (see, Liu et al. Plant Cell 10:1391-1406 (1998)), AtCBL1 expression must have activated more than one signaling pathway. Hence, AtCBL1 is an upstream component in multiple stress response pathways. As illustrated in FIG. 5, multiple stress signals utilize Ca2+ as a second messenger that in turn activates (and also induces the level of) AtCBL1. AtCBL1 interacts with its target proteins including CIPKs (see, Shi et al. *Plant Cell* 11:2393-2405 (1999); Kim et al. Plant Physiol. 124:1844-1853 (2000)). CIPKs and possibly other targets transmit the signal further downstream to transcriptional factors that activate expression of stress genes including DREB1A and DREB2A transcriptional factors. DREB1A and DREB2A activate the expression of target genes including RD29A. Activation of stress genes leads to tolerance to stress conditions in plants.

The present invention is applicable to a wide variety of plants. The invention has wide application in agriculture. For example, enhanced expression of genes of the invention is useful to increase plant tolerance to such events as drought or freeze. Controlling or enhancing expression of the genes is useful to generate new varieties of plants that may demonstrate higher yields and greater tolerance to adverse weather conditions such as drought or freeze.

The present invention is based, at least in part, on the discovery of novel CBL nucleic acids encoding CBL polypeptides that are effective in modulating a stress response in a plant.

II. Isolation of CBL Nucleic Acids

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

The isolation of CBL nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as roots, and a cDNA library which contains the CBL gene transcript is prepared from the mRNA. Alternatively, cDNA may be prepared from mRNA extracted from other tissues in which CBL genes or homologs are expressed.

The cDNA or genomic library can then be screened using a probe based upon the sequence of a cloned CBL gene disclosed here. Probes may be used to hybridize with genomic DNA or cDNA sequences to isolate homologous genes in the same or different plant species. Alternatively, antibodies raised against a CBL polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the CBL genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), Academic Press, San Diego (1990).

Appropriate primers and probes for identifying CBL sequences from plant tissues are generated from comparisons of the sequences provided here with other related genes. Using these techniques, one of skill can identify conserved regions in the nucleic acids disclosed here to prepare the appropriate primer and probe sequences. Primers that specifically hybridize to conserved regions in CBL genes can be used to amplify sequences from widely divergent plant species.

Standard nucleic acid hybridization techniques using the conditions disclosed above can then be used to identify full length cDNA or genomic clones.

III. Inhibition of CBL Activity or Gene Expression

Since CBL genes are involved in controlling a response to stress, it may be desirable under some circumstances to inhibit or decrease CBL activity. However, as those of skill in the art will readily understand, it normally is preferable to increase expression of CBL genes in plants in order to enhance stress response pathways.

A. Inhibition of CBL Gene Expression

The nucleic acid sequences disclosed here can be used to design nucleic acids useful in a number of methods to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants, and the antisense strand of RNA is produced. In plant cells, it has been suggested that antisense suppression can act at all levels of gene regulation including suppression of RNA translation (see, Bourque, *Plant Sci.* (Limerick) 105: 125-149 (1995); Pantopoulos In Progress in *Nucleic Acid Research and Molecular Biology,* Vol. 48. Cohn, W. E. and K. Moldave (Ed.). Academic Press, Inc.: San Diego, Calif., USA; London, England, UK. p. 181-238; Heiser et al. *Plant Sci* (Shannon) 127: 61-69 (1997)) and by preventing the accumulation of mRNA which encodes the protein of interest, (see, Baulcombe, *Plant Mol. Bio.* 32:79-88 (1996); Prins et al., *Arch. Virol* 141: 2259-2276 (1996); Metzlaff et al. *Cell* 88: 845-854 (1997), Sheehy et al. *Proc. Nat. Acad. Sci. USA*, 85:8805-8809 (1988), and Hiatt et al. U.S. Pat. No. 4,801, 340).

The nucleic acid segment to be introduced generally will be substantially identical to at least a portion of the endogenous CBL gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about 5,000 full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress CBL gene expression. The targets can include, for instance, the coding regions, introns, sequences from exon/intron junctions, 5' or 3' untranslated regions, and the like.

Another well known method of suppression is sense cosuppression. Introduction of nucleic acids configured in the sense orientation has been recently shown to be an effective means by which to block the transcription of target genes. For an example of the use of this method to modulate expression of endogenous genes (see, Assaad et al. *Plant Mol. Bio.* 22: 1067-1085 (1993); Flavell, *Proc. Natl. Acad. Sci. USA* 91: 3490-3496 (1994); Stam et al. *Annals Bot.* 79: 3-12 (1997); Napoli et al. *The Plant Cell* 2:279-289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

Oligonucleotide-based triple-helix formation can also be used to disrupt CBL gene expression. Triplex DNA can inhibit DNA transcription and replication, generate site-specific mutations, cleave DNA, and induce homologous recombination (see, e.g., Havre et al., *J. Virology* 67:7324-7331 (1993); Scanlon et al. *FASEB J.* 9:1288-1296 (1995); Giovannangeli et al. *Biochemistry* 35:10539-10548 (1996); Chan et al., *J. Mol. Medicine* (Berlin) 75: 267-282 (1997)). Triple helix DNAs can be used to target the same sequences identified for antisense regulation.

Catalytic RNA molecules or ribozymes can also be used to inhibit expression of CBL genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao et al., *Nature* 365:448-451 (1993); Eastham et al, *J. Urology* 156:1186-1188(1996); Sokol et al., *Transgenic Res.* 5:363-371 (1996); Sun et al. *Mol. Biotechnology* 7:241-251 (1997); and Haseloff et al. *Nature*, 334: 585-591 (1988).

B. Modification of Endogenous CBL Genes

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Alternatively, homologous recombination can be used to induce targeted gene disruptions by specifically deleting or altering the CBL gene in vivo (see, generally, Grewal and Klar, *Genetics* 146: 1221-1238 (1997) and Xu et al. *Genes Dev.* 10: 2411-2422 (1996)). Homologous recombination has been demonstrated in plants (Puchta et al. *Experientia* 50:277-284 (1994); Swoboda et al. *EMBO J.* 13: 484-489 (1994); Offringa et al. *Proc. Natl. Acad. Sci. USA* 90: 7346-7350 (1993); and Kempin et al. *Nature* 389:802-803 (1997)).

In applying homologous recombination technology to the genes of the invention, mutations in selected portions of a CBL gene sequence (including 5' upstream, 3' downstream, and intragenic regions) may be made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91: 4303-4307 (1994); and Vaulont et al. *Transgenic Res.* 4: 247-255 (1995) are conveniently used to increase the efficiency of selecting for altered CBL gene expression in transgenic plants. The mutated gene will interact with the target wild-type gene in such a way that homologous recombination and targeted replacement of the wild-type gene will occur in transgenic plant cells, resulting in suppression of CBL activity.

Alternatively, oligonucleotides composed of a contiguous stretch of RNA and DNA residues in a duplex conformation with double hairpin caps on the ends can be used. The RNA/DNA sequence is designed to align with the sequence of the target CBL gene and to contain the desired nucleotide change. Introduction of the chimeric oligonucleotide on an extrachromosomal T-DNA plasmid results in efficient and specific CBL gene conversion directed by chimeric molecules in a small number of transformed plant cells. This method is described in Cole-Strauss et al. *Science* 273:1386-1389 (1996) and Yoon et al. *Proc. Natl. Acad. Sci USA* 93: 2071-2076 (1996).

The endogenous CBL genes can also be inactivated using recombinant DNA techniques by transforming plant cells with constructs comprising transposons or T-DNA sequences. The CBL mutants prepared by these methods are identified according to standard techniques.

C. Other Means for Inhibiting CBL Activity

CBL activity may be modulated by eliminating the proteins that are required for CBL cell-specific gene expression. Thus, expression of regulatory proteins and/or the sequences that control CBL gene expression can be modulated using the methods described here.

Another strategy is to inhibit the ability of a CBL protein to interact with itself or with other proteins. This can be achieved, for instance, using antibodies specific to CBL. In this method cell-specific expression of CBL-specific antibodies is used to inactivate functional domains through antibody:antigen recognition (see, Hupp et al. *Cell* 83:237-245 (1995)). Alternatively, dominant negative mutants of CBL can be prepared. Use of dominant negative mutants to inactivate target genes is described in Mizukami et al. *Plant Cell* 8:831-845 (1996).

IV. Use of Nucleic Acids of the Invention to Enhance CBL Gene Expression

In many if not most instances, it is desirable to enhance CBL gene expression or provide increased amounts of the CBL gene product in a plant cell. Isolated sequences prepared as described herein can also be used to introduce expression of a particular CBL nucleic acid to enhance or increase endogenous gene expression. For instance, enhanced expression can be used to increase a stress response pathway activity. Normally, it is believed that increased stress response activity increases a plant's ability to withstand successfully such stresses as hyperthermic, hypothermic, hyperosmotic, hypoosmotic stresses, etc. as well as wounding.

Where overexpression of a gene is desired, the desired gene from a different species may be used to decrease potential sense suppression effects.

One of skill will recognize that the polypeptides encoded by the genes of the invention, like other proteins, have different domains which perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

V. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens,* and other transcription initiation regions from various plant genes known to those of skill. Such genes include for example, ACT11 from *Arabidopsis* (Huang et al. *Plant Mol. Biol.* 33:125-139 (1996)); Cat3 from *Arabidopsis* (GenBank No. U43147, Zhong et al. *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol* 208:551-565 (1989)), and Gpc2 from maize (GenBank No. U45855, Manjunath et al., *Plant Mol. Biol.* 33:97-112 (1997)).

Alternatively, the plant promoter may direct expression of the CBL nucleic acid in a specific tissue or may be otherwise under more precise environmental or developmental control. Examples of environmental conditions that may effect transcription by inducible promoters include anaerobic conditions, elevated temperature, or the presence of light. Alternatively, promoter sequences from genes in which expression is controlled by exogenous compounds can be used. For instance, the promoters from glucocorticoid receptor genes can be used (Aoyama et al., *Plant J.* 11:605-12 (1997)). Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Examples of suitable tissue specific promoters include the promoter from LEAFY (Weigel et al. *Cell* 69:843-859 (1992)).

In addition, the promoter sequences from the CBL genes disclosed here can be used to drive expression of the CBL polynucleotides of the invention or heterologous sequences. The sequences of the promoters are identified below.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide tolerance, particularly antibiotic resistance, such as resistance to kanamycin, G418, bleomycin, hygromycin, or herbicide resistance, such as resistance to chlorosulfuron or Basta.

VI. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983). In planta transformation procedures can also be used (Bechtold et al. *Comptes Rendus de l'Academie des Sciences Serie III Sciences de la Vie*, 316:1194-1199 (1993)).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. If antisense or other techniques are used to control gene expression, Northern blot analysis can be used to screen for desired plants. Plants can be screened, for instance, by monitoring response to a stress such as heat, cold, osmotic shock, etc. Exemplary assays are discussed in the Examples below. These procedures will depend, part on the particular plant species being used, but will be carried out according to methods well known to those of skill in the art.

EXAMPLES

The following examples are offered to illustrate, but not to limit the claimed invention.

Example 1

Material and Methods

Generation of AtCBL1 Expression Construct and *Arabidopsis* Transformation:

To make AtCBL1 overexpression construct, the full length AtCBL1 cDNA (Kudla et al. *Proc. Natl. Acad. Sci. USA* 96:4718-4723 (1999)) was digested with Not I and cloned in a pATC940 vector (Ni et al. *Plant J.* 7:661-676 (1995)). The orientation and the junction of the cloned fragment was confirmed by restriction digestion, PCR, and DNA sequencing. This construct was transferred into *Agrobacterium tumefaciens* GV3101 pMP9 strain and used for *Arabidopsis* transformation. *Arabidopsis* (ecotype Columbia GL) plants were grown in a greenhouse under long-day conditions (16 h/8 h light/dark cycle) for 4 weeks and used for transformation as described previously (Bechtold et al. *C.R. Acad. Sci. Paris, Life Sci.* 316:1194-1199 (1993); Clough et al., *Plant J.* 16:735-743 (1998)). Briefly, *Agrobacterium* strain was grown in the LB broth for 24 hours at 30° C. The cells were collected by centrifugation and resuspended in infiltration media (½×MS, 5% sucrose, 1× Gamborg's vitamins, 0.044 µM BAP and 0.04% Silwet L77) to an OD600 between 1.5-2.0. Plants were dipped in this suspension for 30 seconds and transferred to a greenhouse. Seeds were harvested from these plants and screened on selection medium (½×MS, 1× Gamborg's vitamins and 50 µg/ml kanamycin) for transformants. The putative transformants were rescued from plates and grown in the greenhouse under long day conditions.

Stress treatments: *Arabidopsis* (ecotype Columbia GL) seeds were surface sterilized and plated on ½×MS agar medium and grown at 22° C. for three weeks. Wounding treatment was performed by puncturing leaves with hemostat needles. For ABA, salt, and mannitol treatment, 20 ml of the solution containing ABA (100 µM), salt (NaCl, 300 mM), and mannitol (300 mM), respectively, was added to a plate with plants growing in it. Water was added to a plate as a control treatment. Cold treatment was conducted by transferring plants from 22° C. to 4° C. For each stress treatment, plants were kept under stress conditions until harvesting at various time points as indicated below.

Protein isolation and western blot analysis: Leaves of three week old *Arabidopsis* plants were ground to a fine powder in liquid nitrogen with a pestle and mortar and transferred to a centrifuge tube containing extraction buffer (50 mM Tris-HCl, pH 7.4, 100 mM NaCl, 1% Triton-X100, 2 mM EDTA, 2 mM PMSF, 5 µg/ml of leupeptin, aprotinin, and pepstatin). The suspension was mixed thoroughly for 30 seconds and centrifuged at 14,000×g for 30 minutes at 4° C. The supernatant was used as total protein extract and analyzed by SDS-PAGE and western blot. Recombinant AtCBL1 was expressed and antisera was generated as described previously (Kudla et al. *Proc. Natl. Acad Sci. USA* 96:4718-4723 (1999); Shi et al. *Plant Cell* 11:2393-2405 (1999)). Proteins in the gel were electrically blotted to nitrocellulose membrane (Nitrobind, Osmonics). Membranes were blocked with TBST ( 25 mM Tris-HCl pH 7.5, 137 mM NaCl and 0.2% Tween-20) containing 5% nonfat dry milk for at least 4 hours and incubated with affinity purified polyclonal AtCBL1 antibody (1:1000) for 2 hours in TBST containing 1% nonfat dried milk. After multiple washes with TBST, bound antibodies were detected with peroxidase-conjugated secondary antibodies and a chemiluminescence kit (Amersham-Pharmacia).

RNA isolation and northern blot analysis: Total RNA from *Arabidopsis* seedlings was isolated and analyzed according to previously described procedures (Chomczynski et al., *Anal. Biochem.* 162:156-159(1987); Deswal et al. *Eur. J. Biochem.* 267:3181-3188(2000)). Briefly, 10 µg total RNA from each sample was resolved by electrophoresis in a 1.2% agarose gel, transferred to Genescreen plus nylon membrane, prehybridized and hybridized at 65° C. with a 32P labeled DNA probe. The blot was washed and autoradiographed on the Kodak-XR50 film. The images were processed using a scanner and Adobe Photoshop program.

Evaluation of stress tolerance in plants: The T3 generation seeds of vector control (pATC940) and AtCBL1-expressing transgenic plants were surface sterilized and plated on ½ MS agar medium containing a defined concentration of NaCl or mannitol. After 4 days of incubation at 4° C. (for synchronized germination by vernalization), the plates were transferred to growth room (16 hours light and 8 hours dark cycle at 22° C.). Seed germination and overall growth was monitored regularly and photographs were taken using a Kodak digital camera or a video camera attached to a dissecting microscope (Zeiss Stemi SV11).

Example 2

AtCBL1 Protein is Highly Inducible by Stress Conditions and Abscisic Acid

Figure 1:
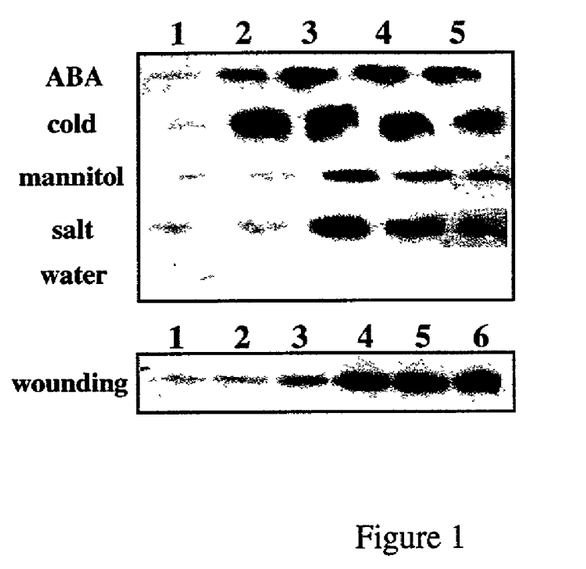

To determine whether AtCBL1 protein is inducible by stress conditions, the *Arabidopsis* plants were treated with a number of stress factors including cold, salt, mannitol, and wounding. The plants were also treated with a "stress hormone", abscisic acid (ABA) that often serves as a chemical signal for various stress conditions especially osmotic stress (Yamaguchi-Shinozaki et al., *Plant Cell* 6:251-264 (1994)). All these treatments significantly induced AtCBL1 protein accumulation although the induction kinetics of AtCBL1 protein varied for each treatment (FIG. 1). The level of AtCBL1 protein increased several fold after 4 hours treatment by ABA and cold and reached the maximum at 24 hours and 8 hours, respectively. After mannitol and salt treatment, the AtCBL 1 protein level increased within 8 hours and peaked at 8 hours and 18 hours. Compared to ABA, salinity, cold, and osmotic (mannitol) stress, induction of AtCBL1 protein by wounding was more rapid (within 1 hour) and peaked at 8 hours. Like mRNA induction (Kudla et al. *Proc. Natl. Acad. Sci. USA* 96:4718-4723 (1999)), protein induction was also transient. After reaching a maximal induction, the AtCBL1 protein level slowly decreased except for wounding stress treatment in which we detected global protein degradation beyond 8 hours after treatment. As a negative control, treatment with water did not induce AtCBL1 protein. To address the specificity of AtCBL1 induction by stress factors and ABA, heat shock samples were included in the analysis. The results indicated no induction of AtCBL1 protein by heat shock.

Figure 2:
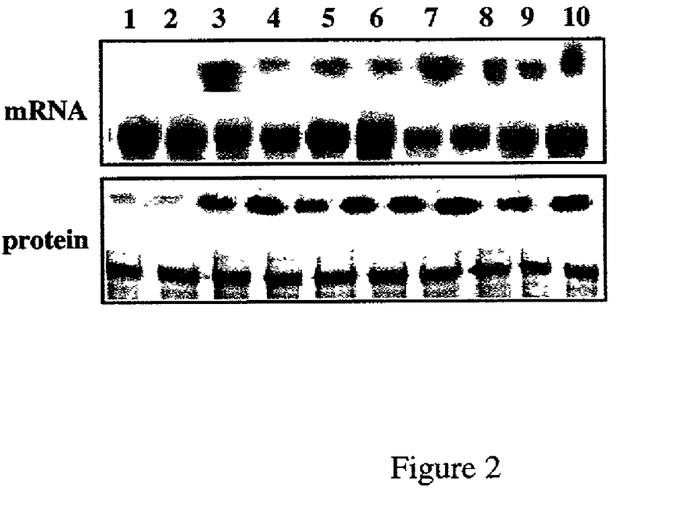
FIG. 2 demonstrates elevation of AtCBL1 mRNA and protein levels in the transgenic plants. (a) mRNA levels of AtCBL1 was examined in the control (lanes 1 and 2) and in the eight independent AtCBL1-expressing lines (lanes 3-10). (b) AtCBL1 protein levels in control (lanes 1 and 2) and AtCBL1-expressing lines (3-10) as revealed by western blot analysis using AtCBL1 affinity purified antibody.
Figure 3:
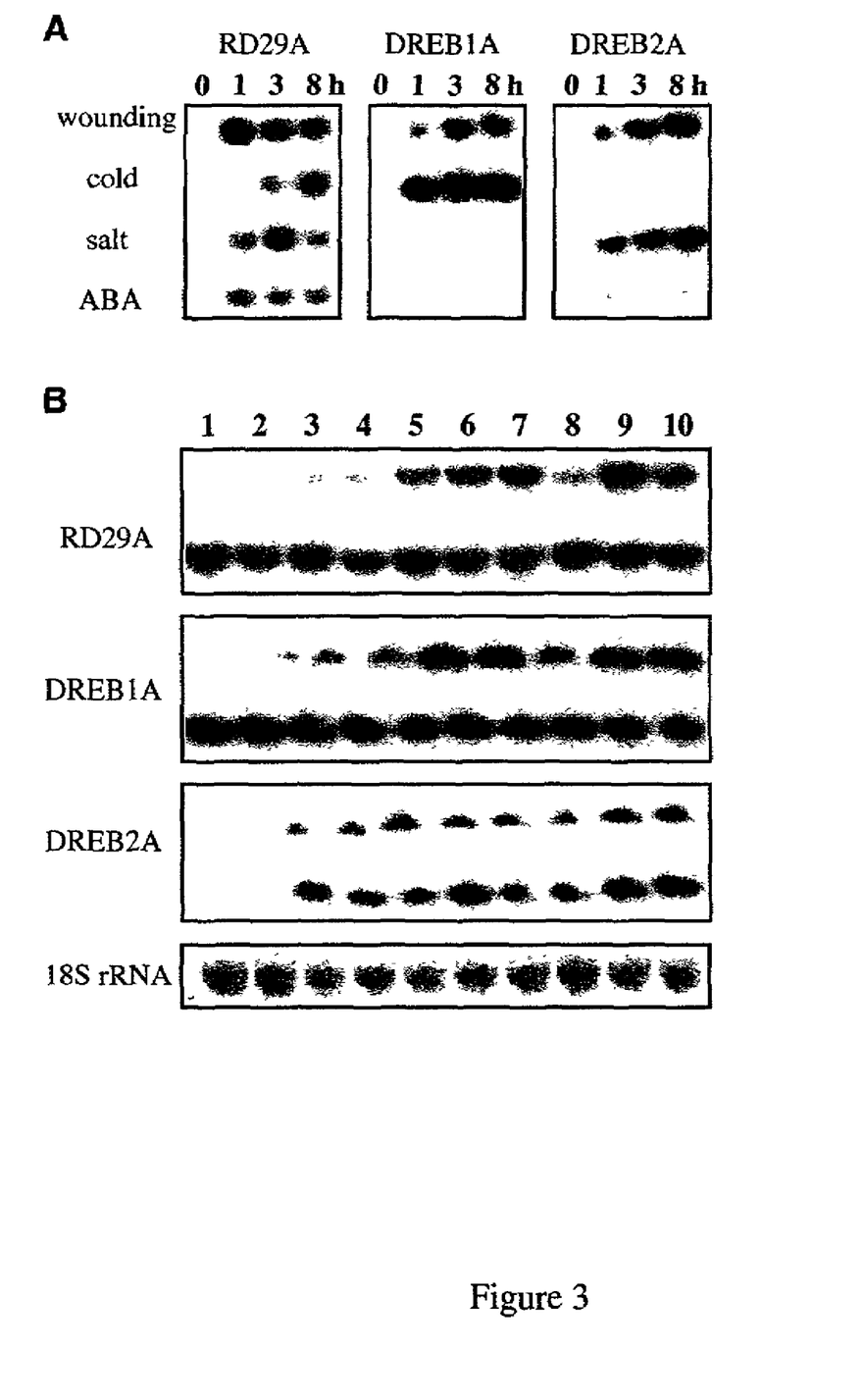

AtCBL1 overexpression does not "over-induce" stress gene markers. As shown in FIGS. 2 and 3, RD29A, DREB1A and DREB2A were expressed at a very similar level in control and AtCBL1-expressing plants after cold treatment. This indicates that AtCBL1 expression merely switches on the pathway but does not alter the "amplitude" of the pathway. This also explains the results from another study where overexpression of pathogen-inducible CaM isoforms constitutively activates the pathogen response pathway leading to enhanced pathogen resistance in the plants (Heo et al. Proc. Natl. Acad. Sci. USA 96:766-771 (1999)). This hypothesis is further supported by the functional specificity of different isoforms of calcium sensors studied. In the case of CaM function in pathogen resistance (Heo et al. Proc. Natl. Acad. Sci. USA 96:766-771 (1999)), only the pathogen-inducible isoforms, but not other isoforms, confer resistance when overexpressed in plants. The present results indicate that AtCBL1 but not other isoforms such as AtCBL4/SOS4 confer stress-tolerance to plants. In both cases, the basal level of calcium sensors is very low under normal conditions and highly inducible by corresponding stress signals. Levels of both calcium and its sensor proteins may be important threshold parameters in calcium-mediated signal transduction in plants. Such a phenomenon has not been examined in animal systems.

AtCBL1-expressing plants display dramatically higher tolerance to salinity and osmotic stress as compared to control plants. Because stress tolerance is such an important trait in agriculture, many earlier studies have utilized various genes to produce stress-tolerant transgenic plants (Holmberg et al., Trends Plant Sci. 3:61-66 (1998)). For example, overexpression of DELTA-1-pyrroline-5-carboxylate synthetase increases proline level, a major osmolyte, and renders plants more tolerant to salt and osmotic stress (Kishor et al. Plant Physiol. 108:1387-1394 (1995)). More recently, it was shown that overexpression of transcriptional factors such as DREB1A, DREB2A, and CBF1 (Liu et al. Plant Cell 10:1391-1406 (1998); Jaglo-Ottosen et al. Science 280:104-106 (1998)) constitutively activates a number of stress genes and leads to tolerance to even broader stress conditions such as salt, drought, and freezing. Manipulation of transcriptional factors has been widely appraised for its efficiency in engineering tolerance to broad spectrum of stress conditions (including cold, salinity and drought). Even greater tolerance could be engineered by overexpressing more than one transcriptional factor at a time. For instance, if DREB1A and DREB2A that function in cold and dehydration pathway, respectively (Liu et al. Plant Cell 10:1391-1406 (1998)), are overproduced in the same plants, these plants demonstrate tolerance to broader stress conditions compared to overexpression of one transcriptional factor alone. The instant invention demonstrates that AtCBL 1-expressing plants possess such increased tolerance. Thus, it is apparent that AtCBL1 expression activates more than just DREB1A and DREB2A but other stress-responsive transcriptional factors as well. Together, these transcriptional factors activate a large number of target stress genes. Therefore, AtCBL 1-expressing plants display a dramatic tolerance to stress conditions. Expressing such CBL genes as AtCBL1 will produce stress-tolerant crops and tremendously benefit agriculture.

In an earlier report (Kudla et al. *Proc. Natl. Acad. Sci. USA* 96:4718-4723 (1999)), AtCBL1 transcript was shown to be inducible by several stress conditions including drought, cold, and wounding. This induction pattern suggests that stress signals may regulate the protein level of AtCBL1. Increase in AtCBL1 protein level may play a role in stress response pathways. Some plant genes are highly induced at mRNA level but not at protein level (Jonak et al. *Proc. Natl. Acad. Sci. USA* 93:11274-11279 (1996); Zhang et al., *Proc. Natl. Acad. Sci USA* 95:7225-7230 (1998)). AtCBL1, as a protein sensor of $Ca^{2+}$, must be changed at protein level in order to alter $Ca^{2+}$ signal transduction.

Example 3

Elevation of AtCBL1 Protein Level in *Arabidopsis* Activates Stress Response Pathways Transgenic *Arabidopsis* plants were produced by introducing AtCBL1 cDNA in sense orientation under the control of a strong constitutive promoter (Ni et al. *Plant J.* 7:661-676 (1995)) via *Agrobacterium* mediated transformation. A total of 30 kanamycin resistant plants were selected from T0 seeds, and T1 generation seeds were collected after selfing. To obtain homozygous AtCBL1 lines, T2 plants were grown and T3 generation seeds were collected. Out of 20 T3 homozygous transgenic lines, 8 lines were selected for further characterization. The AtCBL1 mRNA and protein levels were analyzed by northern and western blot. All eight independent lines showed significantly increased mRNA and protein level as compared to the vector control lines (see, FIG. 2).

To examine whether AtCBL1 overexpression has any effect on stress response pathways in transgenic plants, the expression patterns of a stress gene marker RD29A in the control and AtCBL1-expressing lines were monitored. RD29A (responsive to dessication) gene has been shown to be responsive to ABA, drought, cold, salinity and wounding in the previous studies (Yamaguchi-Shinozaki and Shinozaki, *Plant Cell* 6:251-264 (1994)). The regulation of RD29A gene in the wild type background (ecotype Columbia GL) used in this study was tested. As shown in FIG. 3A, RD29A gene transcript was not detected in the wild type plant under normal conditions but highly induced by wounding, salt, cold, and ABA treatments. Two vector controls and eight AtCBL1-expressing lines were exposed to cold conditions and the RD29A gene expression pattern in these plants was examined. In control plants, RD29A mRNA was not detectable under normal conditions but accumulated to high levels after cold treatment in these plants (FIG. 3B). Interestingly, all AtCBL1-expressing plants produced high levels of RD29A mRNA even under normal conditions. Cold treatment did not significantly increase RD29A expression (FIG. 3B). This result indicates that AtCBL1 expression in transgenic plants activated the stress signaling pathways even under "normal" conditions.

To further confirm that stress responses are constantly active in AtCBL1plants, the expression pattern of two other stress gene markers, DREB1A and DREB2A, were examined. As reported earlier by Liu et al. *Plant Cell* 10:1391-1406 (1998), DREB1A is responsive to cold and DREB2A is induced by salinity. FIG. 3A shows that a similar expression pattern of these two genes was observed in the Columbia GL plants. In the vector control plants, DREB1A but not DREB2A, was induced by cold treatment (FIG. 3B). Remarkably, both genes were highly activated in AtCBL1-expressing plants even without stress treatment (FIG. 3B). These gene markers including RD29A, DREB1A, and DREB2A, did not show hyper-induction in the AtCBL1-expressing plants under stress conditions as compared with control plants (FIG. 3).

Example 4

Figure 4:
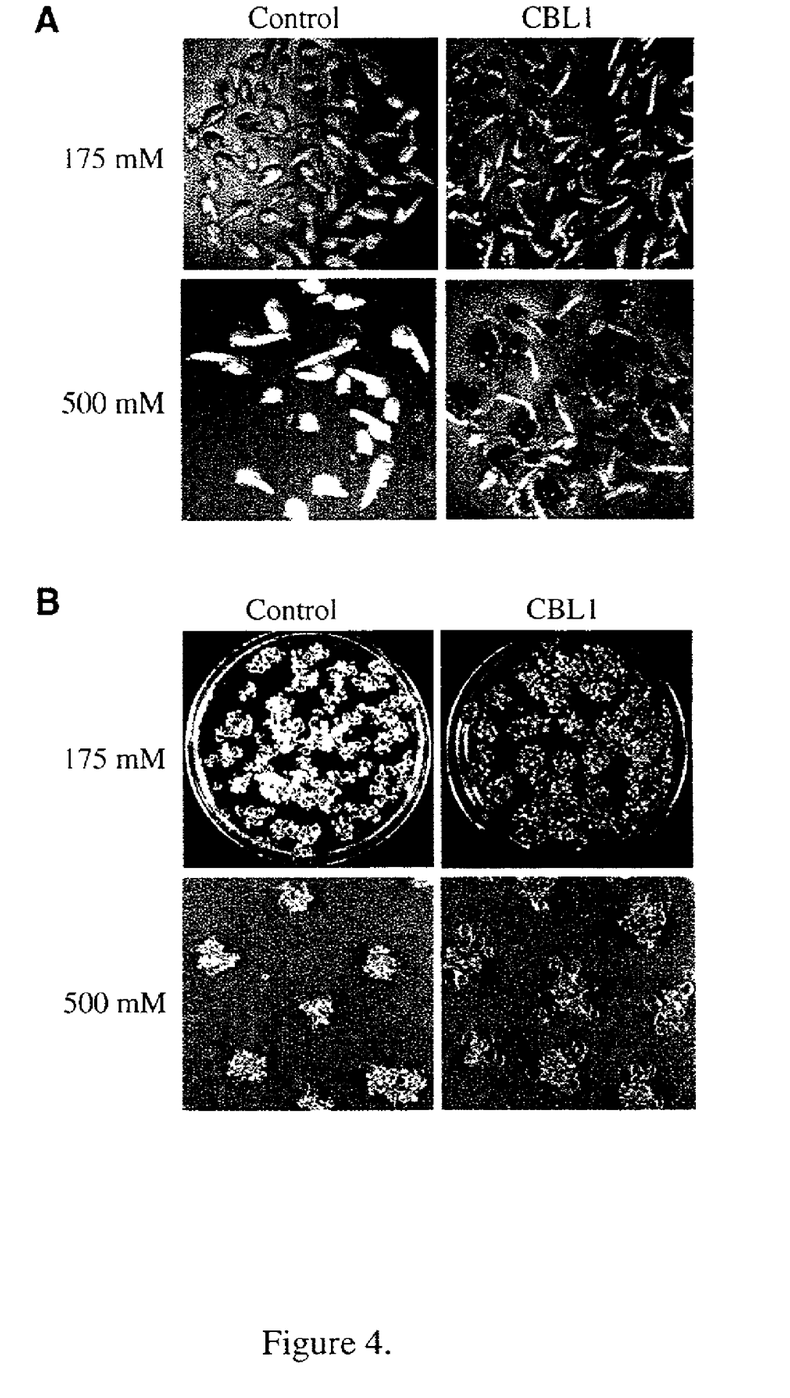
FIG. 4 demonstrates that AtCBL1-expressing plants display dramatically enhanced tolerance to salinity and osmotic stress conditions. (a) Germination of control and AtCBL1-expressing plant seeds on the salt and mannitol medium. Shown here are 5 day-old seedlings. Note cotyledon expansion in the AtCBL1-expressing but not in the control plants. (b) 21-day old seedlings of control and AtCBL1-expressing plants on the stress media. Note the bleaching and root growth inhibition of control plants on salt and mannitol medium, respectively. AtCBL1-expression plants grow well on the same media.

Elevation of AtCBL1 Protein Level in Transgenic Plants Dramatically Increases Tolerance to Salinity and Osmotic Stress Seeds from control and AtCBL1-expressing plants were plated on medium containing various concentrations of salt and mannitol and monitoring their germination and growth. Before the salt and mannitol concentration reached 100 mM and 300 mM, respectively, control and AtCBL1-expressing plants did not show significant difference in germination and growth. FIG. 4A shows that AtCBL1-expressing transgenic seeds germinated much earlier than the control on medium containing 175 mM NaCl or 500 mM mannitol. A dramatic difference in growth and survival was also observed on the same media (FIG. 4B). The AtCBL1-expressing seedlings not only survived much longer but also generated true leaves and formed rosette plants. The control plants never produced true leaves and were largely "bleached" on the salt medium within three weeks. On the high mannitol medium, control plants appeared yellowish and root growth was severely inhibited. In contrast, AtCBL1-expressing plants were dark green and displayed healthy root growth. When higher concentrations of salt (>200 mM) and mannitol (>600 mM) were used, seeds from control or AtCBL1-expressing plants did not germinate within two weeks.

As further confirmation that CBL plays a role in tolerance to stress, targeted disruption of the CBL gene results in decreased tolerance to stress in plants.

It is understood that the examples and embodiments described herein are for illustrative purposes only and that various modifications or changes in light thereof will be suggested to persons of skill in the art and are to be included within the spirit and purview of this application and the scope of the appended claims. All publications, patents, and patent applications cited herein are hereby incorporated by reference.

```
SEQ ID NO: 1
SIZE: 986
SPECIES: Arabidopsis thaliana calcineurin B-like protein 1 (CBL1)
TYPE: DNA 1 tcttttgct gtttctagct cctctctctc tggatctcgc cggcgaaccg tttctcttgg 61 gtgtaaacag tagcaatcaa gctatagaat ctcagatatc gctgaattag ctgttggatt
```

-continued

```
121 ttatccgcct tttcttcgtt atccggggct cgggtataag gtttcatcgt cttatttcat 181 ctgtaaatgg gctgcttcca ctcaaaggca gcaaaagaat ttcgaggaca cgaagaccct 241 gttaagcttg cctctgagac agcttttagt gtgagtgagg ttgaagcatt atttgagcta 301 ttcaagagca taagcagttc ggttgttgat gatggtctga ttaacaagga ggagtttcaa 361 cttgctttgt tcaaaagccg gaagagggag aatatatttg ctaataggat atttgatatg 421 tttgatgtta aacgaaaagg agtcatcgat ttcggggact ttgtaagatc actcaatgtt 481 ttccacccca atgcttctct agaagacaaa atagatttta cgtttaggct ttacgacatg 541 gactgcacgg gttacattga cgacaagag gtcaagcaaa tgttgatcgc gcttctctgc 601 gaatctgaaa tgaaactggc tgatgaaacc atagagataa tactcgataa gacatttgaa 661 gatgcagacg tgaatcaaga tggaaaaatt gataaattag agtggagtga tttcgtaaac 721 aaaaatccat cattgcttaa gatcatgact cttccatatc tcagggatat tacgacaacg 781 tttccgagtt ttgtcttcca ttcggaggtc gatgagattg ccacatgaag aaacaaactg 841 gtttaagacc gagtagattg ccacgagttg gaagaacaag tctgagctaa tcggtgtaat 901 caacatctgt ttgtaaacag tagtagagca tattctcttg aaattgtttg ggttactttt 961 ttcttctcac aacagtttaa aatttt
```

SEQ ID NO: 2
Size: 213
Species: *Arabidopsis thaliana* calcineurin B-like protein 1 (CBL1)
TYPE: PRT

MGCFHSKAAKEFRGHEDPVKLASETAFSVSEVEALFELFKSISSSVVDDG

LINKEEFQLALFKSRKRENIFANRIFDMFDVKRKGVIDFGDFVRSLNVFH

PNASLEDKIDFTFRLYDMDCTGYIERQEVKQMLIALLCESEMKLADETIE

IILDKTFEDADVNQDGKIDKLEWSDFVNKNPSLLKIMTLPYLRDITTTFP

SFVFHSEVDEIAT

---

What is claimed is:

1. A method of enhancing stress tolerance in a plant comprising the step of introducing into the plant an expression cassette comprising a plant promoter operably linked to a heterologous CBL polynucleotide encoding a CBL polypeptide, wherein the CBL polypeptide has the amino acid sequence as shown in SEQ ID NO:2.

2. The method of claim 1, wherein the expression cassette is introduced into the plant through a sexual cross.

3. The method of claim 1, wherein the stress is hypothermia.

4. The method of claim 1, wherein the stress is hyperthermia.

5. The method of claim 1, wherein the stress is hypoosmolarity.

6. The method of claim 1, wherein the stress is hyperosmolarity.

7. The method of claim 1, wherein the stress is drought.

8. The method of claim 1, wherein the expression cassette is functionally integrated into the genome of the plant.

9. A transgenic plant comprising an expression cassette comprising a plant promoter operably linked to a heterologous CBL polynucleotide encoding a CBL polypeptide, wherein the CBL polypeptide has the amino acid sequence as shown in SEQ ID NO:2.

10. The transgenic plant of claim 9, wherein the heterologous CBL polynucleotide is linked to the promoter in an antisense orientation.

* * * * *

SEQUENCE LISTING

<160> NUMBER OF SEQ ID NOS: 2

<210> SEQ ID NO 1
<211> LENGTH: 986
<212> TYPE: DNA
<213> ORGANISM: Arabidopsis thaliana
<220> FEATURE:
<223> OTHER INFORMATION: calcineurin B-like protein 1 (CBL1)

<400> SEQUENCE: 1

```
tcttttgct gtttctagct cctctctctc tggatctcgc cggcgaaccg tttctcttgg     60
gtgtaaacag tagcaatcaa gctatagaat ctcagatatc gctgaattag ctgttggatt   120
ttatccgcct tttcttcgtt atccggggct cgggtataag gtttcatcgt cttatttcat   180
ctgtaaatgg gctgcttcca ctcaaaggca gcaaaagaat ttcgaggaca cgaagaccct   240
gttaagcttg cctctgagac agcttttagt gtgagtgagg ttgaagcatt atttgagcta   300
ttcaagagca taagcagttc ggttgttgat gatggtctga ttaacaagga ggagtttcaa   360
cttgctttgt tcaaaagccg gaagagggag aatatatttg ctaataggat atttgatatg   420
tttgatgtta aacgaaaagg agtcatcgat ttcggggact ttgtaagatc actcaatgtt   480
ttccacccca atgcttctct agaagacaaa atagatttta cgtttaggct ttacgacatg   540
```

-continued

```
gactgcacgg gttacattga acgacaagag gtcaagcaaa tgttgatcgc gcttctctgc    600
gaatctgaaa tgaaactggc tgatgaaacc atagagataa tactcgataa gacatttgaa    660
gatgcagacg tgaatcaaga tggaaaaatt gataaattag agtggagtga tttcgtaaac    720
aaaaatccat cattgcttaa gatcatgact cttccatatc tcaggatat tacgacaacg     780 tttccgagtt tgtcttcca ttcggaggtc gatgagattg ccacatgaag aaacaaactg     840
gtttaagacc gagtagattg ccacgagttg aagaacaag tctgagctaa tcggtgtaat    900
caacatctgt ttgtaaacag tagtagagca tattctcttg aaattgtttg ggttactttt    960
ttcttctcac aacagtttaa aatttt                                         986
```

<210> SEQ ID NO 2
<211> LENGTH: 213
<212> TYPE: PRT
<213> ORGANISM: Arabidopsis thaliana
<220> FEATURE:
<223> OTHER INFORMATION: calcineurin B-like protein 1 (CBL1)

<400> SEQUENCE: 2

```
Met Gly Cys Phe His Ser Lys Ala Ala Lys Glu Phe Arg Gly His Glu
  1               5                  10                  15

Asp Pro Val Lys Leu Ala Ser Glu Thr Ala Phe Ser Val Ser Glu Val
                 20                  25                  30

Glu Ala Leu Phe Glu Leu Phe Lys Ser Ile Ser Ser Ser Val Val Asp
             35                  40                  45

Asp Gly Leu Ile Asn Lys Glu Glu Phe Gln Leu Ala Leu Phe Lys Ser
         50                  55                  60

Arg Lys Arg Glu Asn Ile Phe Ala Asn Arg Ile Phe Asp Met Phe Asp
 65                  70                  75                  80

Val Lys Arg Lys Gly Val Ile Asp Phe Gly Asp Phe Val Arg Ser Leu
                 85                  90                  95

Asn Val Phe His Pro Asn Ala Ser Leu Glu Asp Lys Ile Asp Phe Thr
            100                 105                 110

Phe Arg Leu Tyr Asp Met Asp Cys Thr Gly Tyr Ile Glu Arg Gln Glu
        115                 120                 125

Val Lys Gln Met Leu Ile Ala Leu Leu Cys Glu Ser Glu Met Lys Leu
    130                 135                 140

Ala Asp Glu Thr Ile Glu Ile Ile Leu Asp Lys Thr Phe Glu Asp Ala
145                 150                 155                 160

Asp Val Asn Gln Asp Gly Lys Ile Asp Lys Leu Glu Trp Ser Asp Phe
                165                 170                 175

Val Asn Lys Asn Pro Ser Leu Leu Lys Ile Met Thr Leu Pro Tyr Leu
            180                 185                 190

Arg Asp Ile Thr Thr Thr Phe Pro Ser Phe Val Phe His Ser Glu Val
        195                 200                 205

Asp Glu Ile Ala Thr
    210
```